(12) United States Patent
Phua

(10) Patent No.: US 10,478,839 B2
(45) Date of Patent: Nov. 19, 2019

(54) PORTABLE ULTRAFINE NEBULIZER

(71) Applicant: AIROFOG MACHINERY CO., LTD., Shanghai (CN)

(72) Inventor: Choke Hua Phua, Singapore (SG)

(73) Assignee: AIROFOG MACHINERY CO., LTD., Pujiang Town, Minhang District, Shanghai (CN)

( * ) Notice: Subject to any disclaimer, the term of this patent is extended or adjusted under 35 U.S.C. 154(b) by 0 days.

(21) Appl. No.: 15/326,451

(22) PCT Filed: Feb. 19, 2016

(86) PCT No.: PCT/CN2016/074081
§ 371 (c)(1),
(2) Date: Jan. 13, 2017

(87) PCT Pub. No.: WO2017/020577
PCT Pub. Date: Feb. 9, 2017

(65) Prior Publication Data
US 2018/0207654 A1 Jul. 26, 2018

(30) Foreign Application Priority Data
Aug. 3, 2015 (CN) .................. 2015 2 05764505 U

(51) Int. Cl.
*B05B 7/04* (2006.01)
*B05B 7/06* (2006.01)
(Continued)

(52) U.S. Cl.
CPC ......... *B05B 7/0475* (2013.01); *A01M 7/0021* (2013.01); *A61M 11/002* (2014.02);
(Continued)

(58) Field of Classification Search
CPC ....... B05B 1/3436; B05B 1/3442; B05B 7/00; B05B 7/10; B05B 7/045; B05B 7/0475; B05B 7/2416; A61M 11/06
See application file for complete search history.

(56) References Cited

U.S. PATENT DOCUMENTS 3,255,967 A * 6/1966 Kenney .................... B05B 1/24
239/133
3,472,455 A * 10/1969 Priest .................... A61M 15/00
222/195
(Continued)

FOREIGN PATENT DOCUMENTS

| CN | 2530730 Y | 1/2003 |
|---|---|---|
| CN | 102985188 A | 3/2013 |

(Continued)

*Primary Examiner* — Chee-Chong Lee
*Assistant Examiner* — Joseph A Greenlund
(74) *Attorney, Agent, or Firm* — Global IP Services; Tianhua Gu

(57) ABSTRACT

A portable ultrafine nebulizer comprises a housing, an atomizing nozzle located at the front port of the housing, an air turbine deposited inside the housing, an air flow guide device fixed at the front port of the housing, and a water pump for pumping liquid; the air flow guide device is provided with a plurality of air flow guide blades distributed uniformly around the periphery of the atomizing nozzle, and each of the air flow guide blades is provided with a guide surface; in the atomizing nozzle is provided with a spiral channel and a fluid channel communicated with the water pump, the atomizing nozzle is provided with a spray port at the front end, and the spray port is communicated with the fluid channel through the spiral channel; the air turbine, the air flow guide blades and the spray port are distributed successively along the airflow direction.

5 Claims, 14 Drawing Sheets

Figure 1:
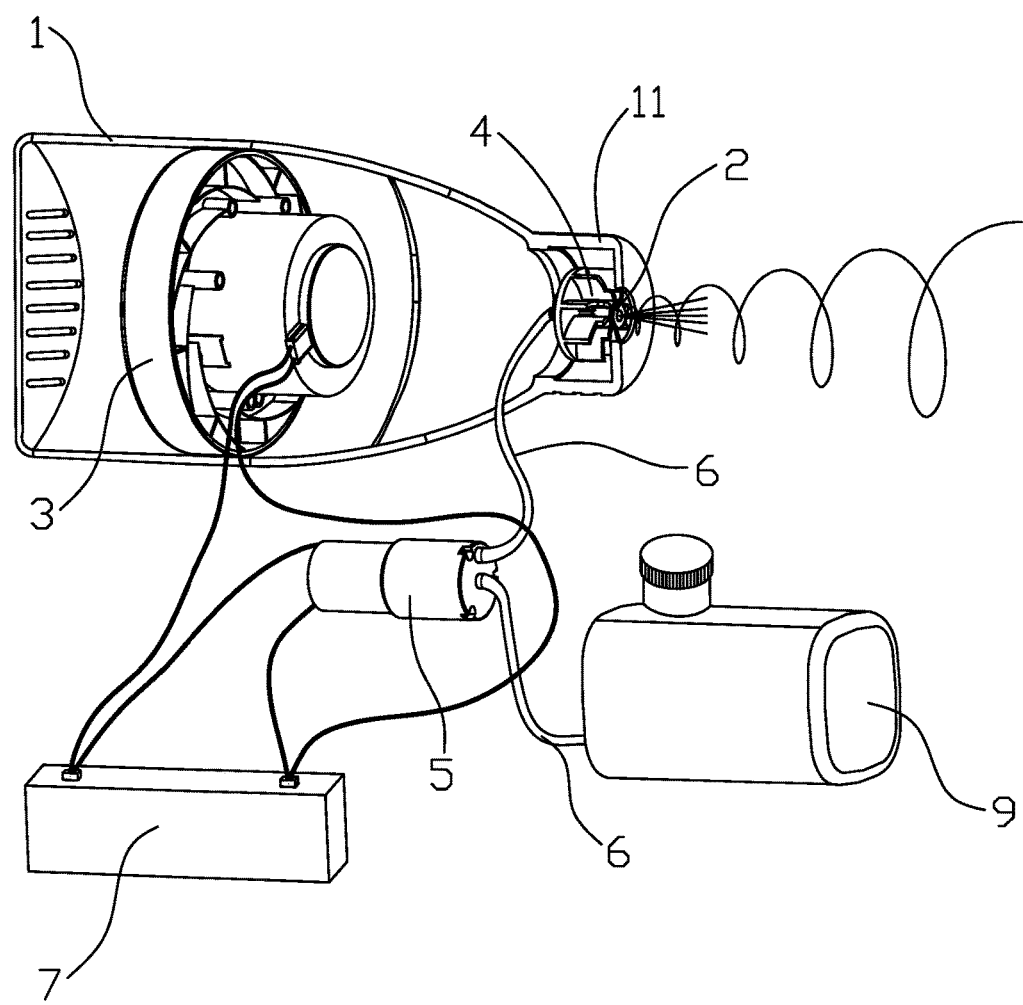
Figure 2:
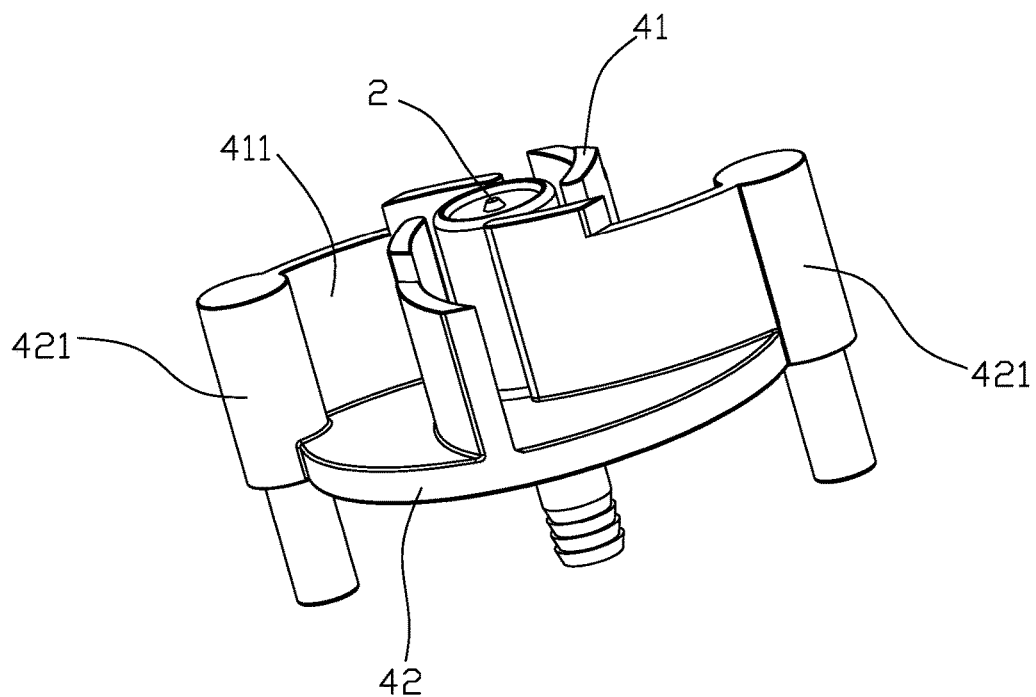
Figure 3:
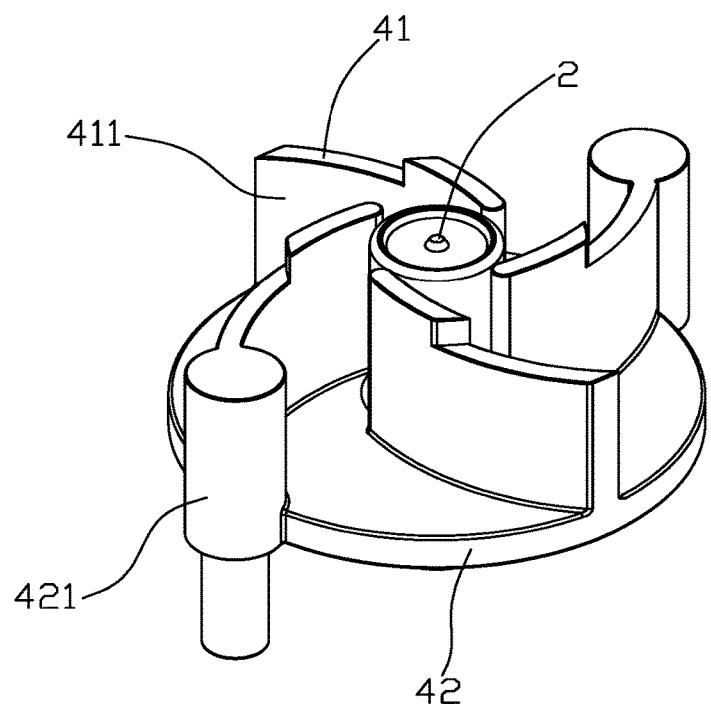
Figure 4:
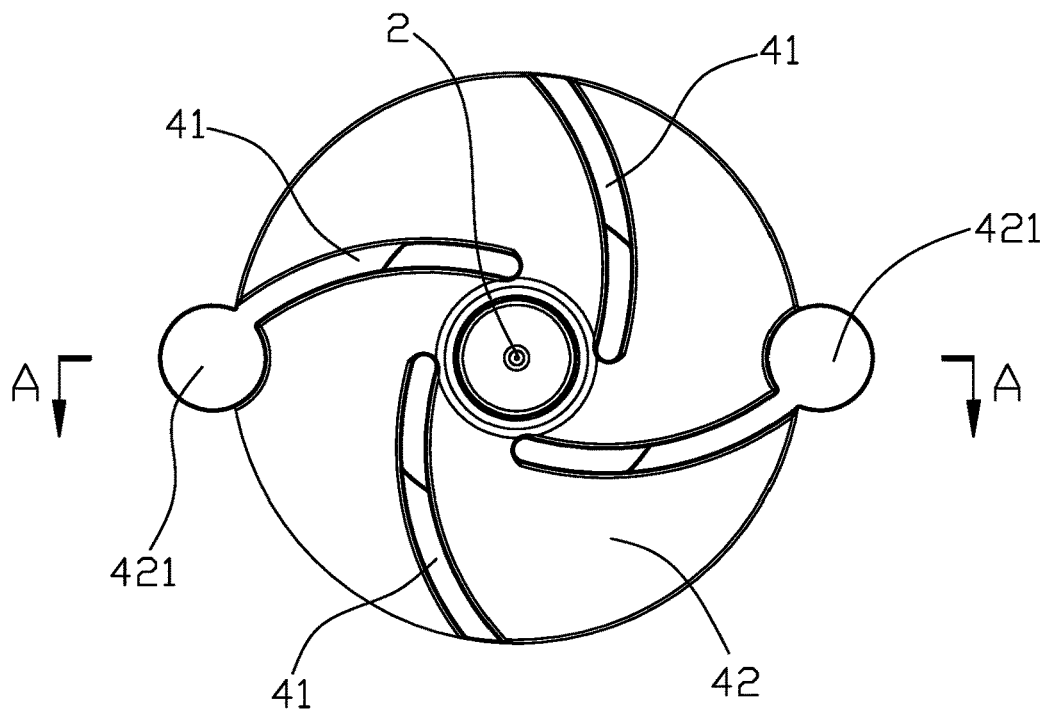

(51) Int. Cl.
  *B05B 7/00* (2006.01)
  *A61M 11/00* (2006.01)
  *A01M 7/00* (2006.01)
  *B05B 7/10* (2006.01)
  *B05B 17/04* (2006.01)
  *B05B 1/34* (2006.01)
  *A61M 11/06* (2006.01)

(52) U.S. Cl.
  CPC ......... *A61M 11/006* (2014.02); *B05B 7/0081* (2013.01); *B05B 7/066* (2013.01); *B05B 7/10* (2013.01); *B05B 17/04* (2013.01); *A61M 11/06* (2013.01); *A61M 2205/8206* (2013.01); *A61M 2206/16* (2013.01); *B05B 1/3436* (2013.01); *B05B 7/045* (2013.01)

(56) References Cited

U.S. PATENT DOCUMENTS

| | | | | |
|---|---|---|---|---|
| 3,901,443 | A * | 8/1975 | Mitsui | B05B 17/0615 239/102.2 |
| 3,970,250 | A * | 7/1976 | Drews | A61M 11/005 239/102.2 |
| 4,018,387 | A * | 4/1977 | Erb | B05B 7/0416 239/405 |
| 4,221,331 | A * | 9/1980 | Goran, Jr. | B05B 3/022 239/121 |
| 4,260,110 | A * | 4/1981 | Werding | B05B 1/3436 239/404 |
| 4,396,152 | A * | 8/1983 | Abplanalp | B05B 7/0458 239/337 |
| 4,986,453 | A * | 1/1991 | Lina | B05B 11/3018 222/321.2 |
| 5,022,587 | A * | 6/1991 | Hochstein | A61M 11/06 128/203.12 |
| 5,110,052 | A * | 5/1992 | Graf | B05B 7/0416 239/333 |
| 5,232,164 | A * | 8/1993 | Resch | B05B 1/265 239/424 |
| 5,385,106 | A * | 1/1995 | Langshaw | A01G 11/00 111/118 |
| 5,388,766 | A * | 2/1995 | Buisson | B05B 1/3436 222/321.2 |
| 5,397,034 | A * | 3/1995 | Wunsch | B05B 15/30 222/333 |
| 5,711,488 | A * | 1/1998 | Lund | B05B 1/3436 239/333 |
| 5,715,999 | A * | 2/1998 | Hsu | B05B 7/0075 222/333 |
| 5,722,598 | A * | 3/1998 | Werding | B05B 1/3405 239/403 |
| 5,992,765 | A * | 11/1999 | Smith | B05B 1/3436 239/337 |
| 6,050,504 | A * | 4/2000 | Schultz | B05B 7/0475 239/327 |
| 6,161,777 | A * | 12/2000 | Carter | A45F 3/16 239/222.11 |
| 6,216,961 | B1 * | 4/2001 | Utter | B05B 7/0075 222/175 |
| 6,371,388 | B2 * | 4/2002 | Utter | B05B 7/0075 239/152 |
| 6,371,389 | B1 * | 4/2002 | Bickart | B05B 1/3436 239/491 |
| 6,619,284 | B2 * | 9/2003 | Kong | A61M 11/06 128/200.11 |
| 6,776,133 | B2 * | 8/2004 | Tezuka | F02N 3/02 123/185.3 |
| 7,384,006 | B2 * | 6/2008 | Hornsby | B05B 15/33 239/333 |
| 7,559,490 | B2 * | 7/2009 | Rappin | B05B 7/2435 239/154 |
| 7,568,635 | B2 * | 8/2009 | Micheli | B05B 3/1014 239/240 |
| 7,878,418 | B2 * | 2/2011 | Sevy | A61M 11/06 128/200.18 |
| 7,938,342 | B2 * | 5/2011 | Octeau | B05B 1/3436 239/333 |
| 8,690,080 | B2 * | 4/2014 | Myers | B05B 1/3421 239/463 |
| 9,421,295 | B1 * | 8/2016 | Li | A61L 9/125 |
| 9,623,426 | B2 * | 4/2017 | Schurle | B05B 1/185 |
| 10,000,330 | B2 * | 6/2018 | Szekely | B65D 83/206 |
| 10,065,202 | B2 * | 9/2018 | Campbell | B05B 7/2416 |
| 10,105,718 | B2 * | 10/2018 | Kim | B05B 11/00 |
| 10,322,424 | B2 * | 6/2019 | Wright | B05B 5/03 |
| 2001/0003353 | A1 * | 6/2001 | Kawamoto | A47K 7/04 239/333 |
| 2005/0194467 | A1 * | 9/2005 | Wanbaugh | B05B 9/0861 239/333 |
| 2008/0029614 | A1 | 2/2008 | Dore | |
| 2008/0061164 | A1 * | 3/2008 | Ciriani | B05B 7/10 239/327 |
| 2008/0265060 | A1 * | 10/2008 | Canfield | B05B 7/2416 239/373 |
| 2010/0133358 | A1 * | 6/2010 | Gohring | B05B 7/0081 239/337 |
| 2010/0187335 | A1 * | 7/2010 | Reedy | B05B 7/2416 239/528 |
| 2011/0073677 | A1 * | 3/2011 | Hahn | B05B 7/0081 239/311 |
| 2012/0217322 | A1 * | 8/2012 | Songbe | B05B 1/3436 239/469 |
| 2015/0151313 | A1 * | 6/2015 | Pastore | A61L 2/22 239/373 |
| 2015/0202638 | A1 * | 7/2015 | Pouliaude | B05B 1/341 239/373 |
| 2016/0010855 | A1 * | 1/2016 | Myers | F23D 11/24 239/403 |
| 2017/0065997 | A1 * | 3/2017 | Burrowes | B05B 11/3084 |
| 2017/0291181 | A1 * | 10/2017 | Wright | B05B 5/03 |
| 2018/0207654 | A1 * | 7/2018 | Phua | B05B 7/0475 |

FOREIGN PATENT DOCUMENTS

| | | |
|---|---|---|
| CN | 103329876 A | 10/2013 |
| CN | 203874934 U | 10/2014 |
| CN | 204994473 U | 1/2016 |

* cited by examiner

PORTABLE ULTRAFINE NEBULIZER

CROSS REFERENCE TO RELATED PATENT APPLICATION

The present application is the US national stage of PCT/CN2016/074081 filed on Feb. 19, 2016, which claims the priority of the Chinese patent application No. 2015205764505 filed on Aug. 3, 2015, which applications are incorporated herein by reference.

BACKGROUND OF THE PRESENT INVENTION

Field of Invention

The present invention relates to a nebulizer, particularly relates to a portable ultrafine nebulizer.

Description of Related Arts

Nebulizer has been widely applied in manufacturing and life, for example, in the fields of vector-control, public health industry, sanitation and hygiene, agriculture, medical science and the like, normally, the nebulizer is adopted for spraying liquid medicine, such that the sprayed liquid medicine has atomizing effect. Meanwhile, the smaller the diameter of the fog particles sprayed by the nebulizer is, the better the atomizing effect is.

A Chinese patent application, with publication No. CN1219351A, has disclosed a high-efficiency electrical interlocking pesticide ultrafine nebulizer. The ultrafine nebulizer has a case, a chemical bottle, a chemical tube, an operating lever, as well as a gas-liquid-electricity combined pipeline, which is connected between the case and a operating handle; the front end of the handle is provided with a gas-liquid-electricity control switch, an inlet of the switch is connected to a pneumatic tube, the chemical pipe, and a wire, which are respectively connected to a gas tank in the case, the chemical bottle and a battery box; an outlet of the gas-liquid-electricity combined pipeline is provided with a chemical output tube and a wire-connected ultrafine atomizer head; the gas tank is connected with a manual aspirated type bladder; the ultrafine atomizer head is composed of a micro-motor, a motor base, a annular sprayer and a ultrafine atomizer plate, the ultrafine atomizer plate features a conical ridge, on which uniform dense brush-like fluffs are provided.

Regarding to the above ultrafine nebulizer in the prior art, the atomization principle thereof is that: the liquid from the chemical output tube is sprayed to the ridge of the ultrafine atomizer plate through several small nozzle orifices of the annular sprayer, the micro-motor drives the ultrafine atomizer plate to rapidly rotate to generate high strength centrifugal force, by which the liquid sprayed by the cyclic sprayer is uniformly crushed and thrown out, such that diffused and free ultrafine fog particles are formed in the ambient air. Since only one stage of atomization is adopted, i.e., the micro-motor is employed to drive the ultrafine atomizer plate to rapidly rotate to generate high strength centrifugal force, by which the liquid sprayed by the cyclic sprayer is uniformly crushed and thrown out, so that the sprayed fog particles has relative large diameter, and the atomizing effect thereof is still poor.

Besides, there are two types of power supply portable ultrafine nebulizers in the market:

The first is driven by an active power (AC, non-battery) motor. The main disadvantage thereof is that: it may affect other electrical equipments along the same power line; also, the power supply has to pass through the active power (e.g., normally a power socket) and a power wire, with the result that the nebulizer may be affected by the limitation of the location of the active power (e.g., power socket), the length of the power wire, and the passed region or objects of the power wire. Therefore, the application range thereof is subject to many limitations.

The second is driven by a battery (i.e., DC). The main disadvantage thereof is that: since the battery power is proportional to the weight of the battery, as for light battery, the service time is short, and no sufficiently large power is supplied for air turbines to generate high air speed/air pressure for atomizing liquid; in case that it is guarantee to have a sufficiently large power, the battery and the air turbine will be relative large and heavy, which is inconvenience for carrying.

SUMMARY OF THE PRESENT INVENTION

In view of the above disadvantages in the prior art, the technical problem to be solved in the present invention is to provide a portable ultrafine nebulizer, which features relative smaller sprayed fog particles and better atomizing effect.

In order to achieve the above objects, the present invention provides a portable ultrafine nebulizer, comprising a housing, an atomizing nozzle located at the front port of the housing; and further comprising an air turbine deposited inside the housing, an air flow guide device fixed at the front port of the housing, and a water pump for pumping liquid; the air flow guide device is provided with a plurality of air flow guide blades distributed uniformly around the atomizing nozzle, and each of the air flow guide blades is provided with a guide surface; in the atomizing nozzle is provided with a spiral channel and a fluid channel communicated with the water pump, the atomizing nozzle is provided with a spray port at the front end, and the spray port is communicated with the fluid channel through the spiral channel; the air turbine, the air flow guide blades and the spray port are distributed successively along the airflow direction.

Preferably, the atomizing nozzle comprises a nozzle housing with an inner cavity, an inner core deposited at the front section of the inner cavity, a first block deposited in the inner cavity and located at the rear of the inner core, and a junction inserted in the rear section of the inner cavity; the junction is connected with the water pump by a transfusion tube, the spray port is placed at the front end of the nozzle housing, the outer wall of the first block is bonded to the inner wall of the nozzle housing, a liquid flow space is formed between the outer wall of the inner core and the inner wall of the nozzle housing, and between the rear end of the inner core and the front end of the first block, respectively; the spiral channel is placed at the outer wall of the inner core, the first block is provided with a first through hole penetrated through forwards and backwards, the junction is provided with a second through hole penetrated through forwards and backwards; the first through hole, the second through hole and the liquid flow space are communicated to form the fluid channel.

Preferably, the nozzle housing has a cylindrical external profile, the spray port comprises an enlarging part, a shrinking part and a collecting part distributed successively along the front-rear direction; the enlarging part is a conic shape with a gradually decrease diameter along the front-rear direction, both the shrinking part and the collecting part are cylindrical shapes extended along the front-rear direction;

the collecting part has a larger diameter than the diameter of the shrinking part, the top of the inner cavity is a conical shape with a gradually increase diameter along the front-rear direction, the front end of the nozzle housing is provided with an annular groove at the periphery of the enlarging part, and the groove has a trapezoid cross section in the radial direction.

Preferably, the nozzle housing has a trumpet-shaped external profile, the spray port comprises the enlarging part and the shrinking part, which are both cylindrical shapes extended along the front-rear direction; the enlarging part has a larger diameter than the diameter of the shrinking part.

Preferably, the atomizing nozzle comprises a nozzle housing with an inner cavity, an inner core deposited at the front section of the inner cavity, and a junction inserted in the rear section of the inner cavity; the junction is connected with the water pump by a transfusion tube, the spray port is placed at the front end of the nozzle housing, the inner core is provided with a receiving hole, which is fixedly provided with a second block; the spiral channel is placed at the inner wall of the inner core and is located between the inner wall of the inner core and the outer wall of the second block; the junction is provided with a second through hole penetrated through forwards and backwards, and the second through hole forms the fluid channel; the front end of the inner core is provided with an enlarging part of inner core and a shrinking part of inner core distributed successively along the front-rear direction; both the enlarging part of inner core and the shrinking part of inner core are cylindrical shapes, and the enlarging part of inner core has a larger diameter than that of the shrinking part of inner core; all of the enlarging part of inner core, the shrinking part of inner core, the spray port and the spiral channel are communicated.

Preferably, the nozzle housing has a cylindrical or trumpet-shaped external profile, the spray port is round, and the diameter of the spray port is larger than that of the enlarging part of inner core.

Further, the air flow guide device comprises a fixed disc, and the air flow guide blade extends forward from the front end surface of the fixed disc; the nozzle housing fixedly penetrates in the center of the fixed disc; the fixed disc is provided with a plurality of connection parts, which are fixedly connected to the housing.

Preferably, the nozzle housing of the atomizing nozzle is threaded connected to the fixed disc of the air flow guide device, or is integral with the fixed disc of the air flow guide device.

Further, the nebulizer also comprises a power supply battery connected with the air turbine and the water pump, and the power supply battery is placed outside the housing.

In order to achieve the above objects, the present invention provides a portable ultrafine nebulizer, comprising a housing and an atomizing nozzle, and further comprising an air pipe fixed at the front port of the housing, an air turbine deposited inside the housing, an air flow guide device fixed at the front port of the air pipe, and a water pump for pumping liquid; the atomizing nozzle is placed at the front port of the air pipe, and the air flow guide device is provided with a plurality of air flow guide blades distributed uniformly around the atomizing nozzle, and each of the air flow guide blades is provided with a guide surface; in the atomizing nozzle is provided with a spiral channel and a fluid channel communicated with the water pump, the atomizing nozzle is provided with a spray port at the front end, and the spray port is communicated with the fluid channel through the spiral channel; the air turbine, the air flow guide blades and the spray port are distributed successively along the airflow direction.

In view of the foregoing, the portable ultrafine nebulizer of the present invention has the following beneficial effects:

In the present invention, liquid is pumped by adopting the water pump, and is sprayed by the atomizing nozzle, so as to achieve the first stage atomization; simultaneously, a revolving airflow generated at the atomizing nozzle by using the air turbine and the air flow guide device, shears the fog particles sprayed by the atomizing nozzle, thereby decreasing the diameter of the atomizing effect, and achieving the second stage atomization; the present invention features better atomizing effect by the two kinds of atomization.

BRIEF DESCRIPTION OF THE DRAWINGS

FIG. 1 is a structural diagram of a portable ultrafine nebulizer in the first embodiment.

FIGS. 2 and 3 are perspective schematic illustrations of a cylindrical atomizing nozzle and an air flow guide device after assembly of different angles.

FIG. 4 is a right view of the cylindrical atomizing nozzle and the air flow guide device after assembly.

FIGS. 5 and 6 are perspective schematic illustrations of a trumpet-shaped atomizing nozzle and an air flow guide device after assembly of different angles.

FIG. 7 is a right view of the trumpet-shaped atomizing nozzle and the air flow guide device after assembly.

FIGS. 8 to 11 are sectional views of the cylindrical atomizing nozzle and the air flow guide device after assembly in different embodiments.

FIGS. 12 to 15 are sectional views of the trumpet-shaped atomizing nozzle and the air flow guide device after assembly in different embodiments.

FIG. 16 is an enlarge view of circle C in the FIG. 8.

FIG. 17 is an enlarge view of circle D in the FIG. 10.

FIG. 18 is an enlarge view of circle E in the FIG. 12.

FIG. 19 is an enlarge view of circle F in the FIG. 14.

FIG. 20 is a sectional view of the cylindrical atomizing nozzle in FIG. 10.

FIG. 21 is a sectional view of the trumpet-shaped atomizing nozzle in FIG. 12.

FIG. 22 shows another embodiment of the portable ultrafine nebulizer of the present application.

FIG. 23 is a structural diagram of the inner of an inner core in FIGS. 8, 9, 12 and 13.

FIG. 24 is an elevation view of FIG. 23.

FIG. 25 is a connection view of an air flow guide device and a connecting lid of the present application.

FIG. 26 shows another embodiment of the portable ultrafine nebulizer of the present application.

REFERENCE NUMERALS

1. housing;
2. atomizing nozzle;
21. spiral channel;
23. spray port;
231. enlarging part;
232. shrinking part;
233. collecting part;
24. nozzle housing;
241. inner cavity;
242. groove;
25. inner core;
252. shrinking part of inner core;

26. first block;
261. first through hole;
27. junction
271. second through hole;
29. second block;
3. air turbine;
4. air flow guide device;
41. air flow guide blade;
411. guide surface;
42. fixed disc;
421. connection part;
5. water pump;
6. transfusion tube;
7. power supply battery;
8. air pipe;
9. liquid case;
272. friction tooth;
251. enlarging part of inner core
11. connection lid
111. air outlet

DETAILED DESCRIPTION OF THE
PREFERRED EMBODIMENTS

Embodiment 1

The embodiment modes of the present invention are described hereunder through specific examples, and persons skilled in the art may easily understand other advantages and efficacies of the present invention from the contents disclosed in the present description.

It should be known that the form, the scale, the size and the like shown in the drawings attached in this specification are all simply used to match with the content exposed by the specification for the skilled in the art understanding and reading, but not used to limit qualifications when the invention may be implemented, thus any modification of structure, alteration of proportional relation, or modulation of size without technical essential meanings shall be fall into the covered scope by the disclosed technical solution of the invention, with no effect to the generated function and achieved objects of the present invention. Meanwhile, terms such as "up", "down", "left", "right" and the like cited in this specification are also simply for clearness of the description but not used to limit the scope implemented by the invention. The change or the adjustment of the relative relation should also be seen as the scope of the invention when there is no substantial alteration in the technical content.

Figure 17:
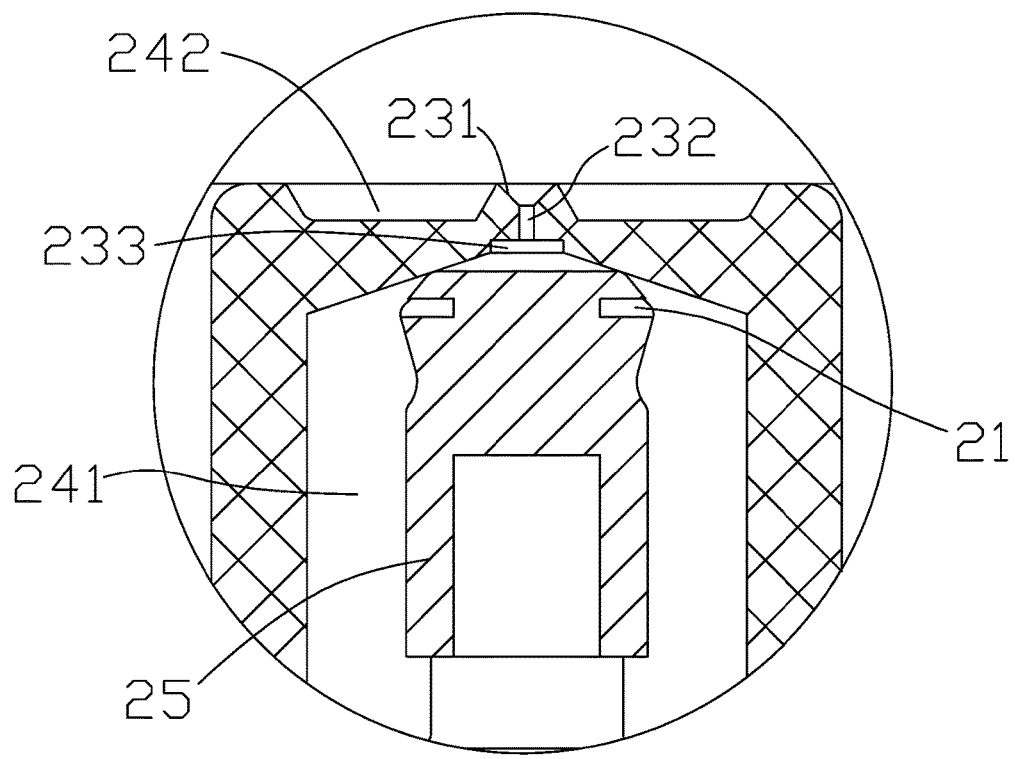
Figure 20:
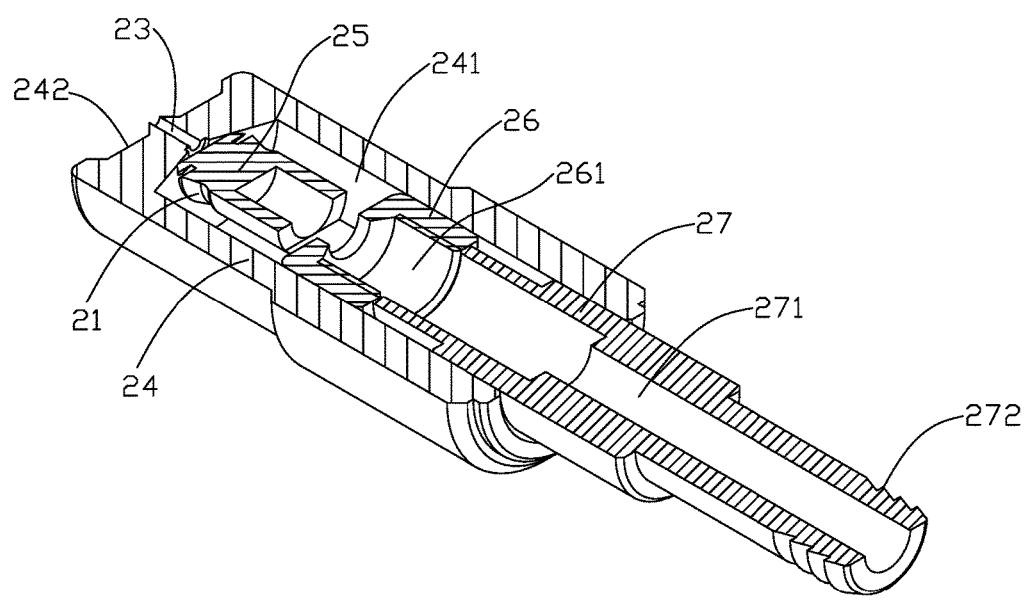

As shown in FIG. 1, the present invention provides a portable ultrafine nebulizer, comprising a housing 1, an atomizing nozzle 2 provided at the front port of the housing 1, an air turbine 3 deposited inside the housing 1, an air flow guide device 4 fixedly placed at the front port of the housing 1, and a water pump 5 connected with a liquid case 9 though a transfusion tube 6. As shown in FIGS. 2 to 7, the air flow guide device 4 is provided with a plurality of air flow guide blades 41 uniformly distributed at the periphery of the atomizing nozzle 2, each of the air flow guide blades 41 is provided with a guide surface 411. As shown in FIGS. 17 and 20, inside the atomizing nozzle 2 is provided with two spiral channels 21, and a fluid channel communicated with the water pump 5 through the transfusion tube 6; the front end of the atomizing nozzle 2 is provided with a spray port 23, which is communicated with the fluid channel though the spiral channel 21; the air turbine 3, the air flow guide blade 41, and the spray port 23 are distributed successively along the airflow direction.

The working principle of the present invention is that: liquid is pumped from the liquid case 9 by the water pump 5, and is then conveyed to the fluid channel of the atomizing nozzle 2 though the transfusion tube 6; liquid flows across the two spiral channels 21 in the atomizing nozzle 2 though the fluid channel to form spiral liquid flow, which finally sprays out from the spray port 23 to generate atomizing effect, thereby achieving a first stage atomization; simultaneously, fast-moving airflow is generated by using the air turbine 3, and forms a revolving airflow under the action of the guide surface 411 of the air flow guide blade 41 as flowing across the air flow guide device 4, then the revolving airflow shears fog particles sprayed from the spray port 23 of the atomizing nozzle 2 for decreasing the diameter of the fog particles, so as to achieve the second stage atomization. After the two kinds of atomization, the present invention has better atomizing effect, and the relative smaller fog particles enable to spray more distantly under the action of the airflow.

As shown in FIGS. 11 and 20, in one embodiment, the atomizing nozzle 2 comprises a nozzle housing 24 provided with an inner cavity 241, an inner core 25 deposited at the front section of the inner cavity 241, a first block 26 deposited in the inner cavity 241 and located at the rear of the inner core 25, and a junction 27 inserted in the rear section of the inner cavity 241. The junction 27 is connected with the water pump 5 by the transfusion tube 6; the spray port 23 is placed at the front end of the nozzle housing 24; an outer wall of the first block 26 is bonded with an inner wall of the nozzle housing 24; liquid flow space is formed between an outer wall of the inner core 25 and an inner wall of the nozzle housing 24, and between the rear end of the inner core 25 and the front end of the first block 26; the spiral channel 21 is placed at the outer wall of the inner core 25. The first block 26 is provided with a first through hole 261 penetrated through forwards and backwards. The junction 27 is provided with a second through hole 271 penetrated through forwards and backwards; the first through hole 261, the second through hole 271 and the liquid flow space are communicated to form the fluid channel. In this embodiment, the pumped liquid from the water pump 5 flows across the second through hole 271, the first through hole 261 and the liquid flow space successively, and then flows into the spiral channel 21 at the outer wall of the inner core 25, to form a spiral liquid flow, which finally sprays from the spray port 23.

In order to make the above atomizing nozzle 2 feature better atomizing function, as shown in FIGS. 2 to 4, in one embodiment, the external profile of the nozzle housing 24 may be cylindrical. Meanwhile, as shown in FIGS. 10, 11 and 17, the spray port 23 comprises an enlarging part 231, a shrinking part 232 and a collecting part 233 distributed successively along the front-rear direction; the enlarging part 231 is a conic show with a gradually decrease diameter along the front-rear direction, both the shrinking part 232 and the collecting part 233 are cylindrical shapes extended along the front-rear direction; the collecting part 233 has a larger diameter than the shrinking part 232, the top of the inner cavity 241 is a conical shape with a gradually increase diameter along the front-rear direction, the front end of the nozzle housing 24 is provided with an annular groove 242 at the periphery of the enlarging part 231, and the groove 242 has a trapezoid cross section in the radial direction. As such, the liquid flowing though the inner core 25, will successively flow though the collecting part 233, the shrinking part 232, and the enlarging part 231, and be pressed into the shrinking part 232 from the collecting part 233, so as to increase water pressure; after the liquid enters the enlarging part 231 from the shrinking part 232, the water pressure of the pressed liquid is reduced, and the liquid is radially sprayed for enlarging the spray area of liquid.

Figure 5:
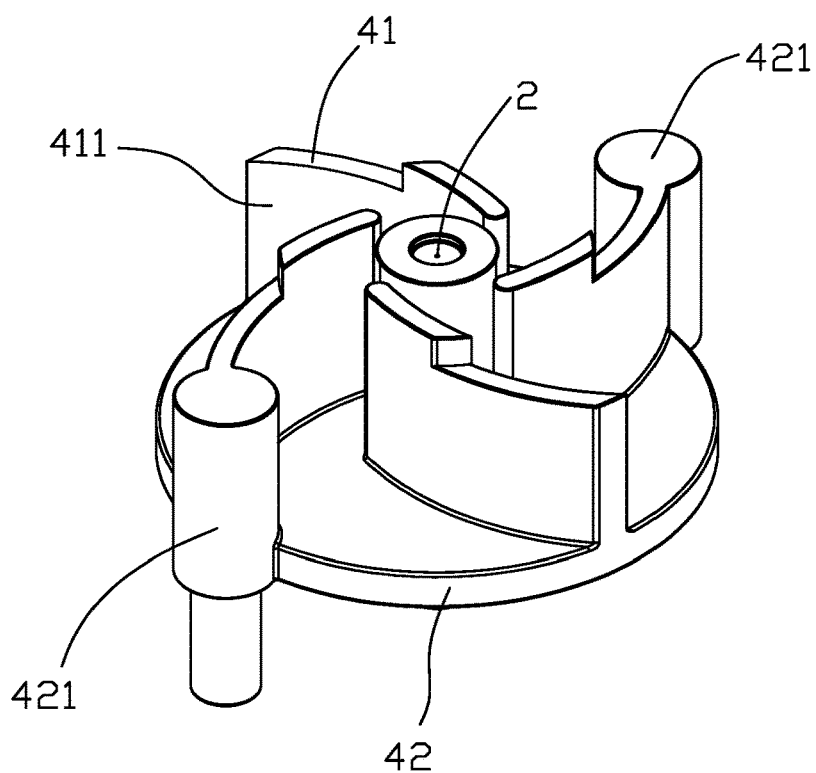
Figure 6:
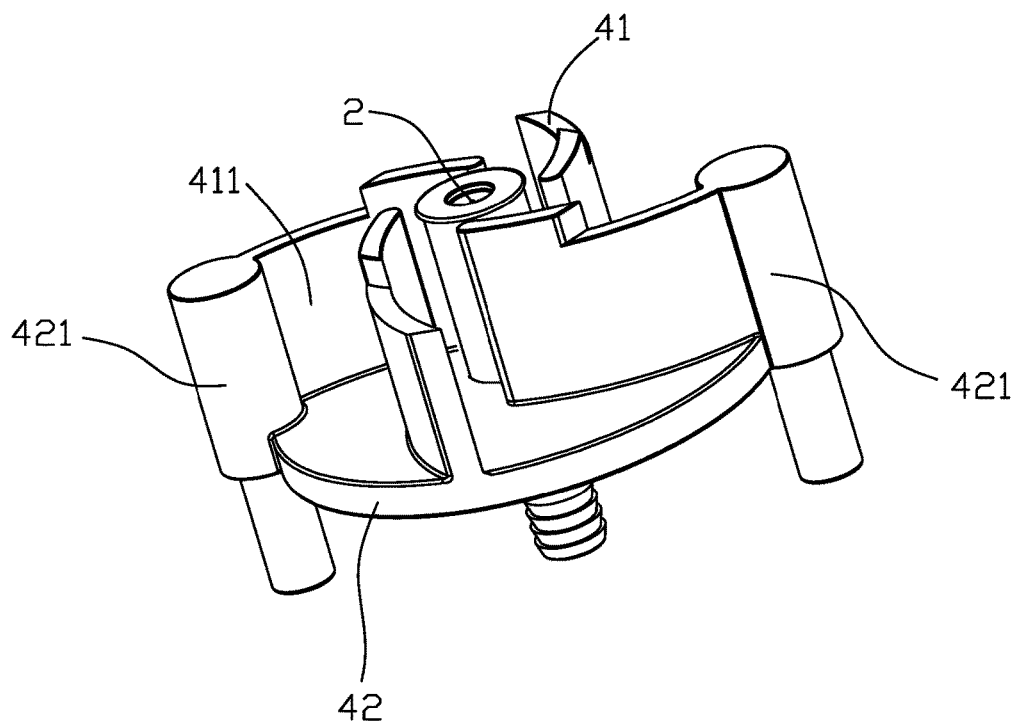
Figure 7:
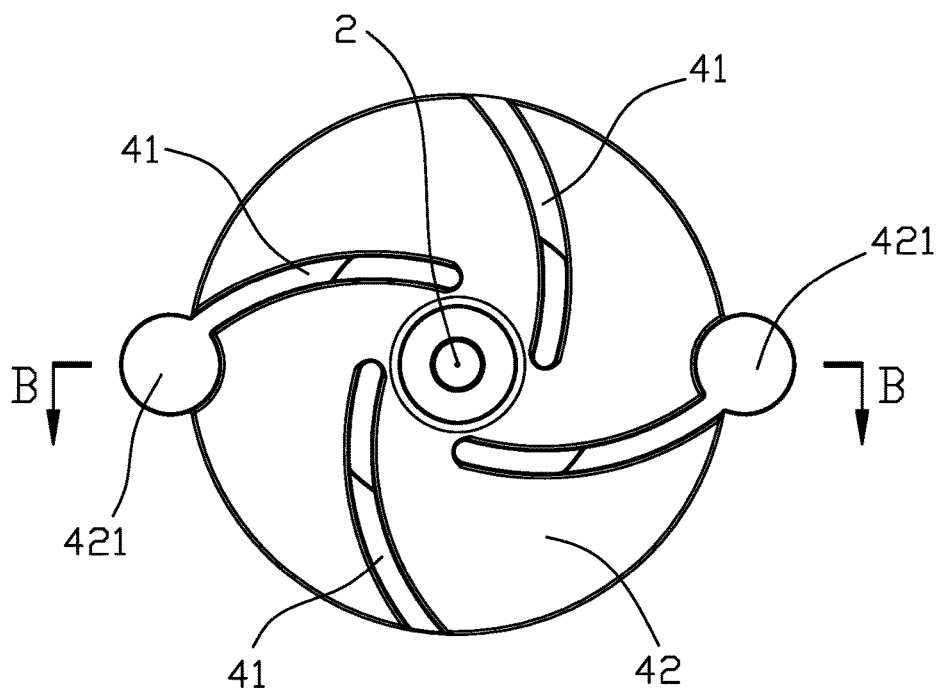
Figure 8:
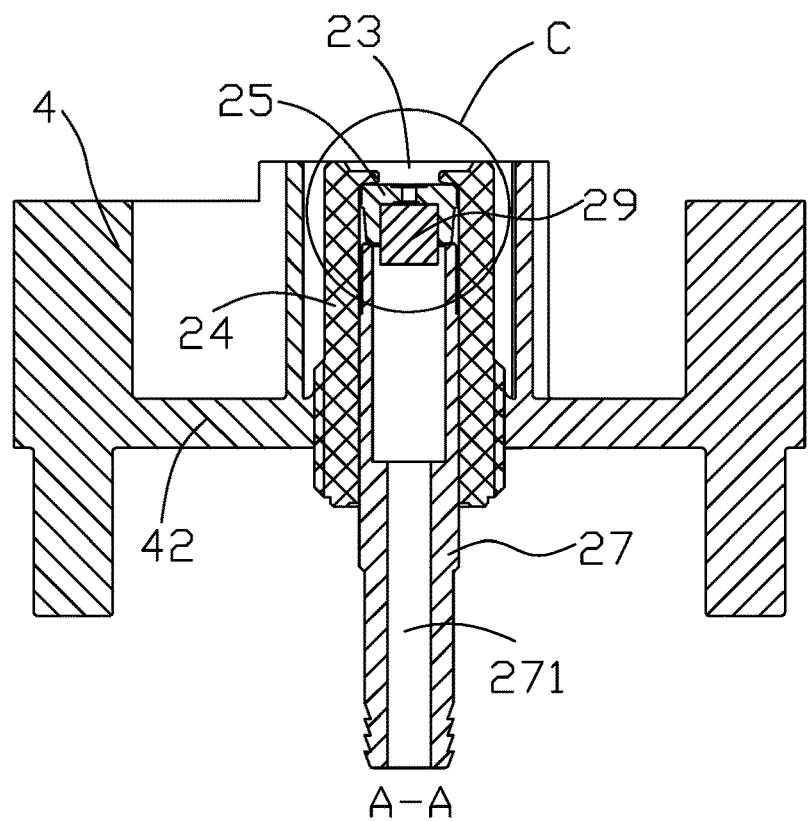
Figure 9:
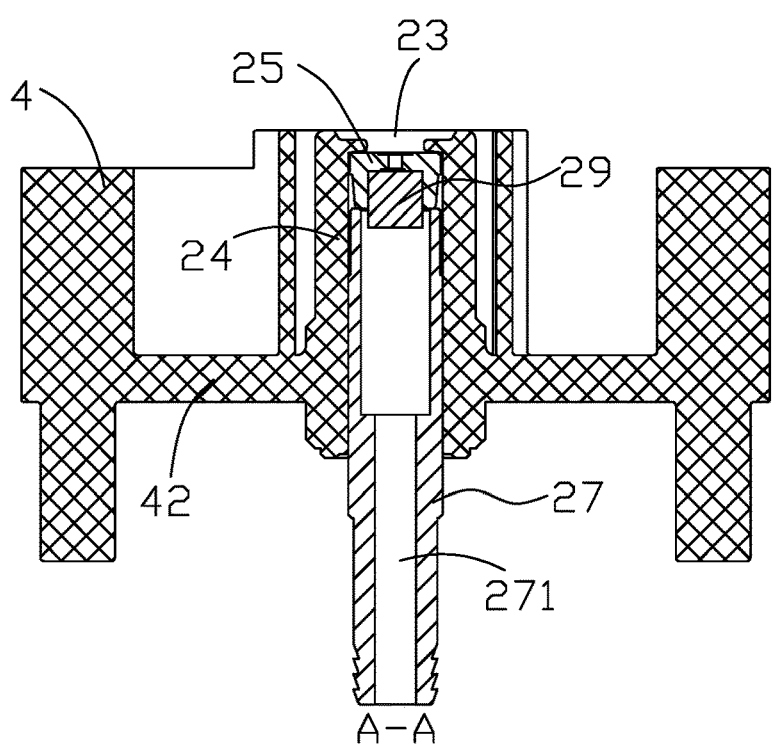
Figure 10:
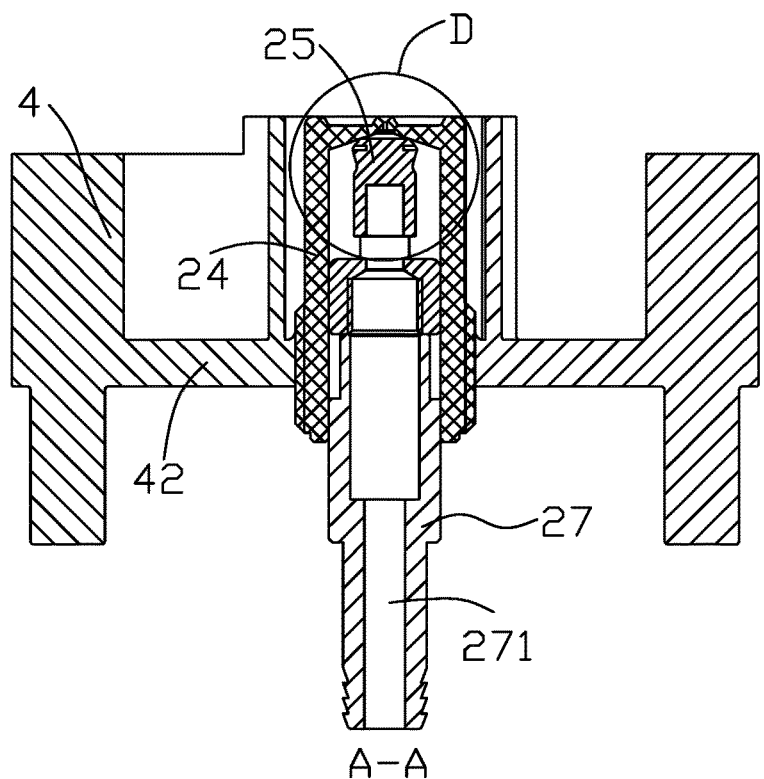
Figure 11:
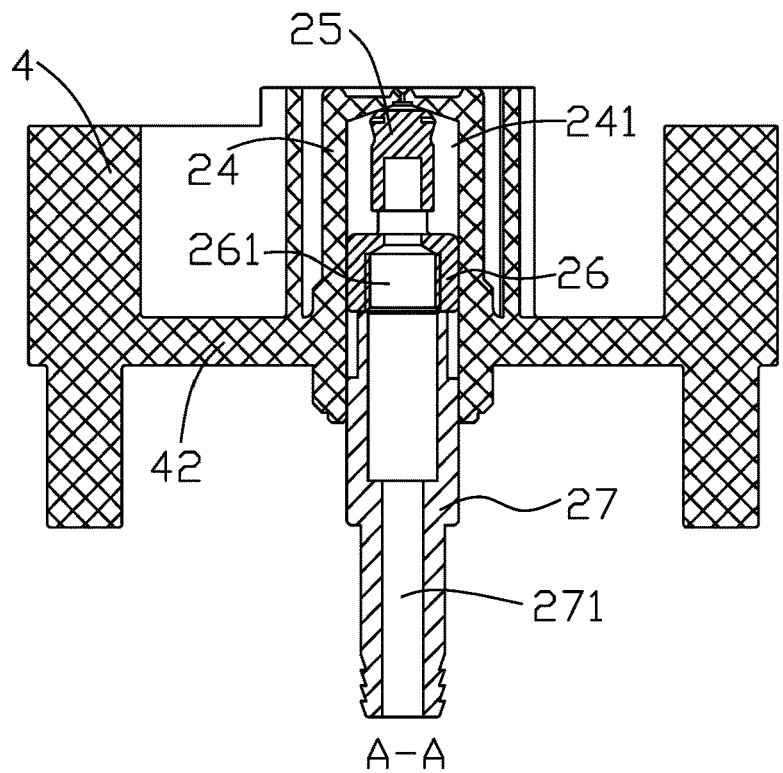
Figure 14:
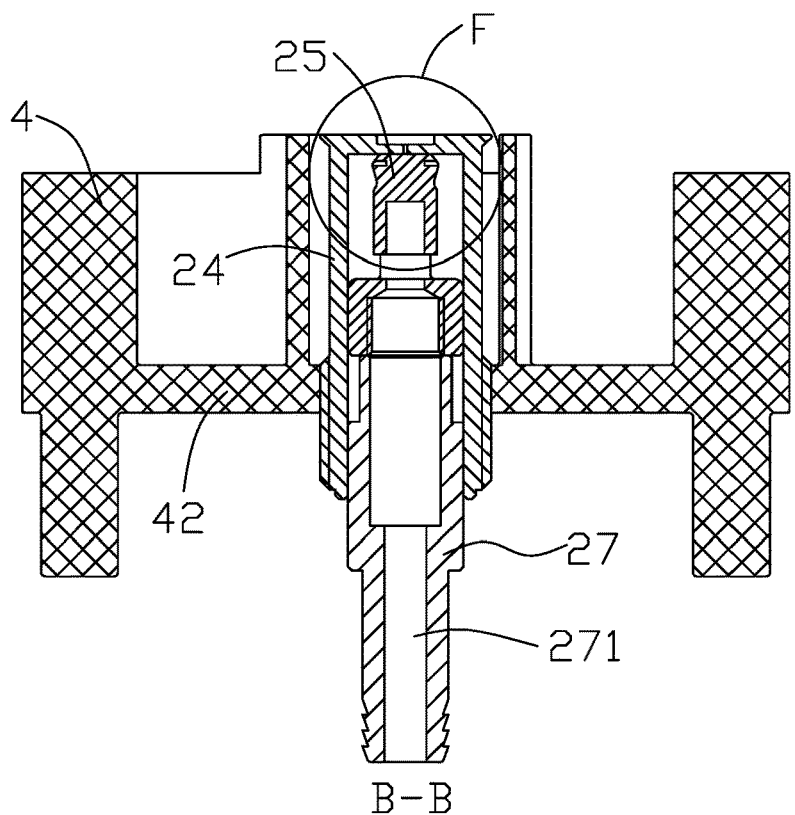
Figure 15:
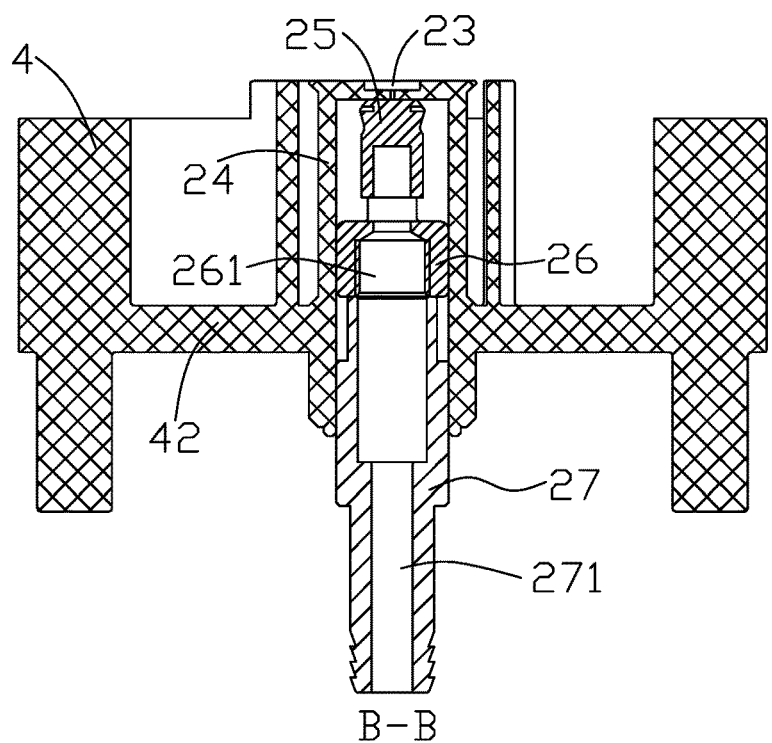
Figure 16:
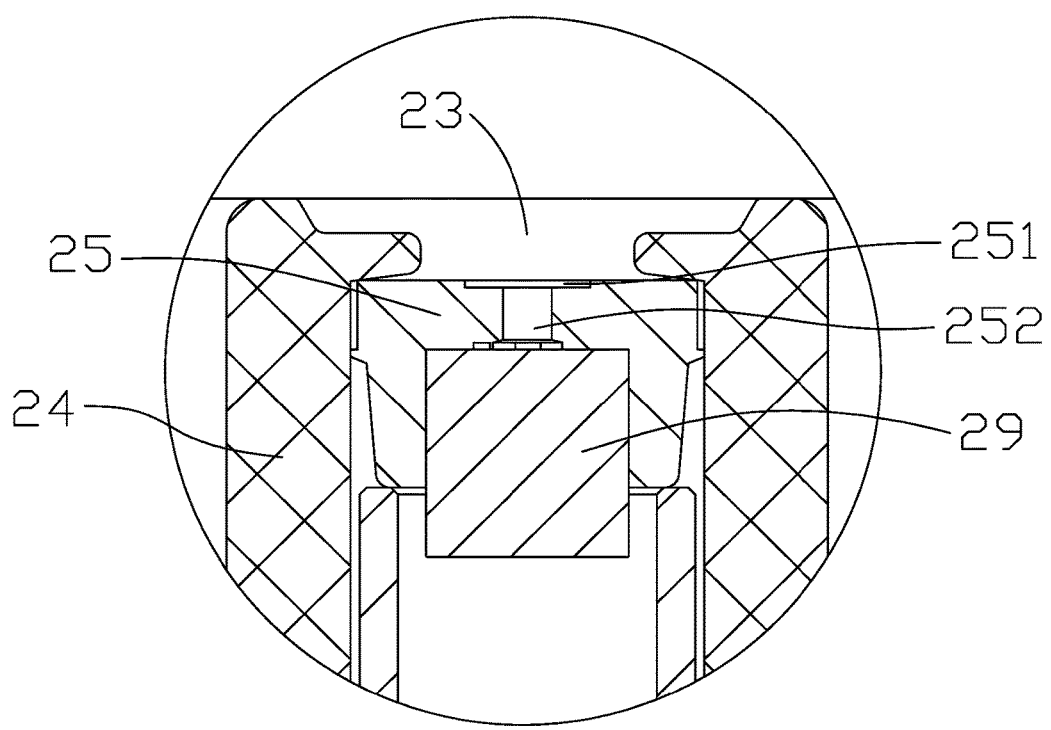
Figure 19:
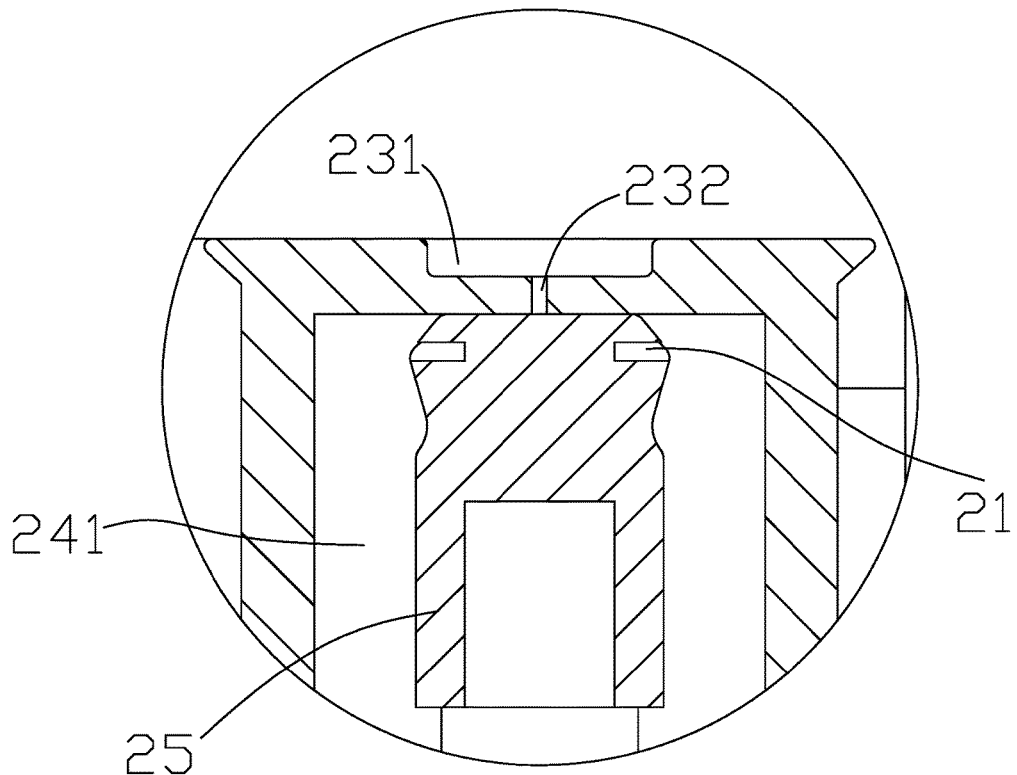

In order to make the above atomizing nozzle 2 feature better atomizing function, as shown in FIGS. 5 to 7, in another embodiment, the external profile of the nozzle housing 24 is trumpet-shaped. Meanwhile, as shown in FIGS. 14, 15 and 19, the spray port 23 comprises the enlarging part 231 and the shrinking part 232 successively distributed in the front-rear direction, which are both cylindrical shapes extended along the front-rear direction; the enlarging part 231 has a larger diameter than the shrinking part 232. As such, the liquid flowing though the inner core 25, will successively flow though the shrinking part 232, and the enlarging part 231, and be pressed into the shrinking part 232, so as to enhance water pressure; after the liquid enters the enlarging part 231 from the shrinking part 232, the water pressure of the pressed liquid is reduced, and the liquid is radially sprayed for enlarging the spray area of liquid. Meanwhile, the trumpet-shaped external profile of the nozzle housing 24 has a certain guiding effect on the sprayed liquid, by which the spray area of the liquid will be larger, and the atomizing effect will be better as a result.

Figure 12:
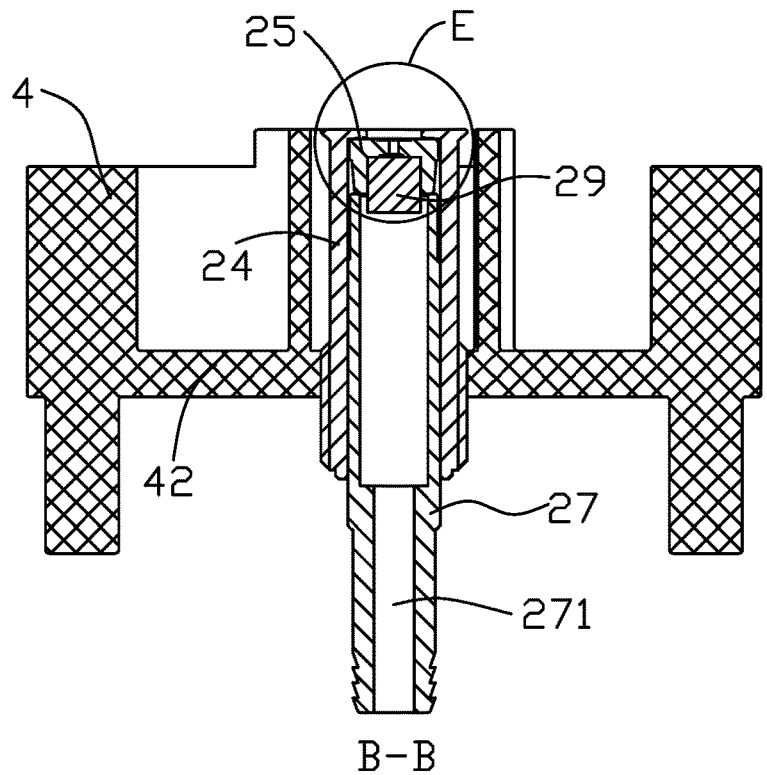
Figure 13:
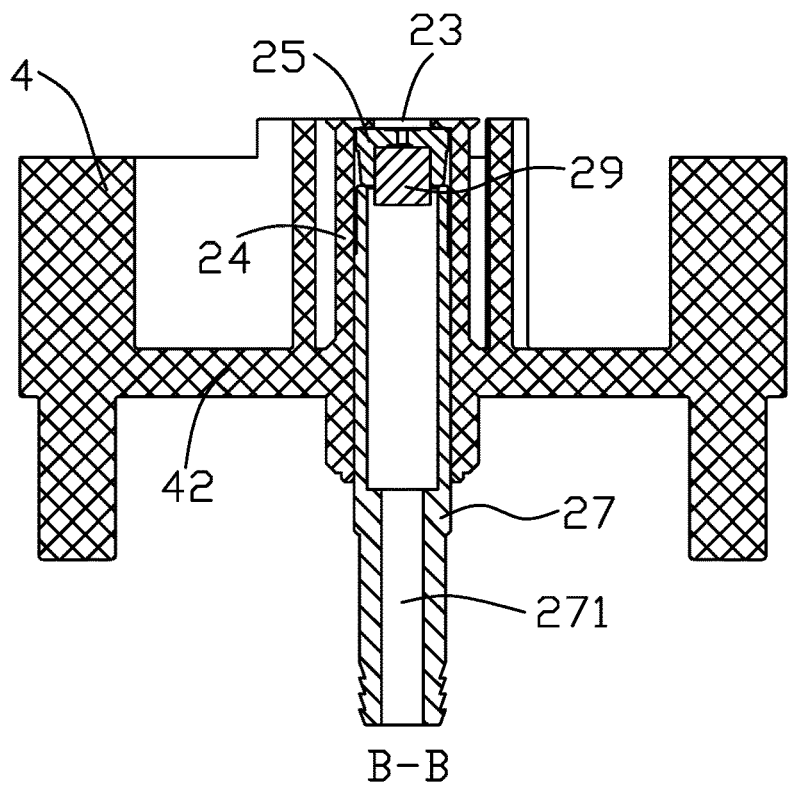
Figure 18:
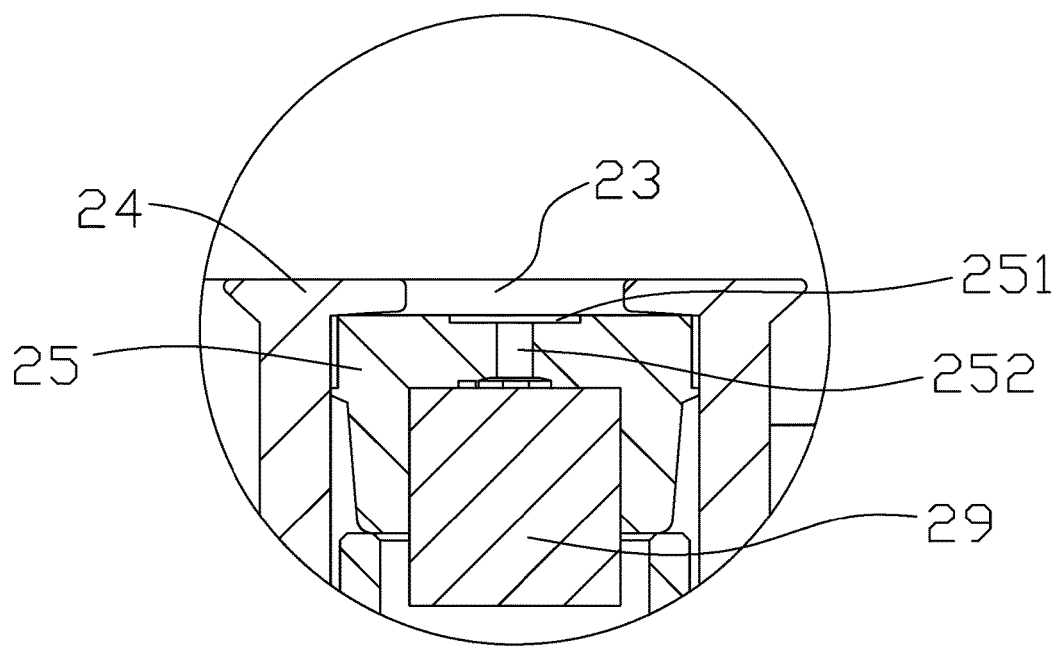
Figure 21:
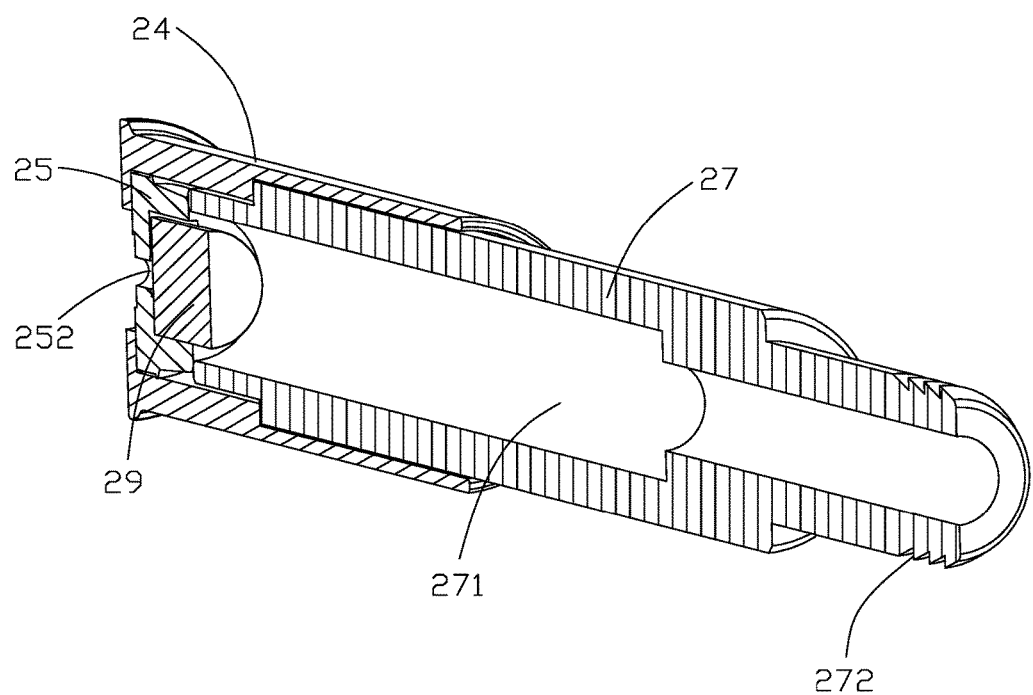
Figure 22:
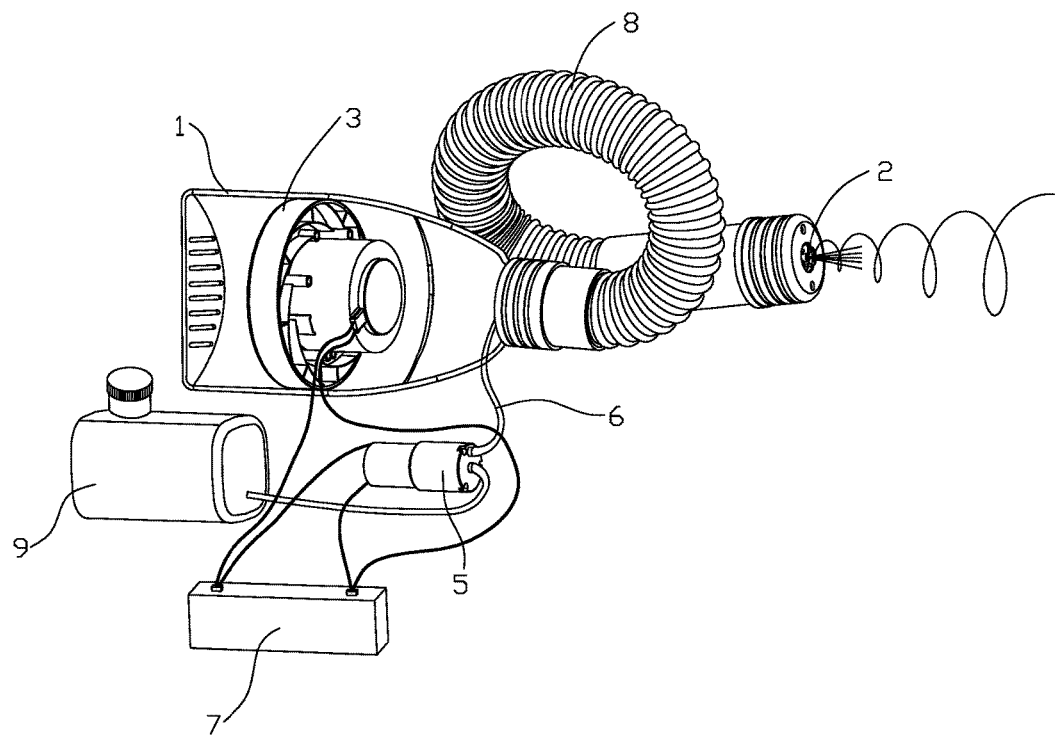
Figure 23:
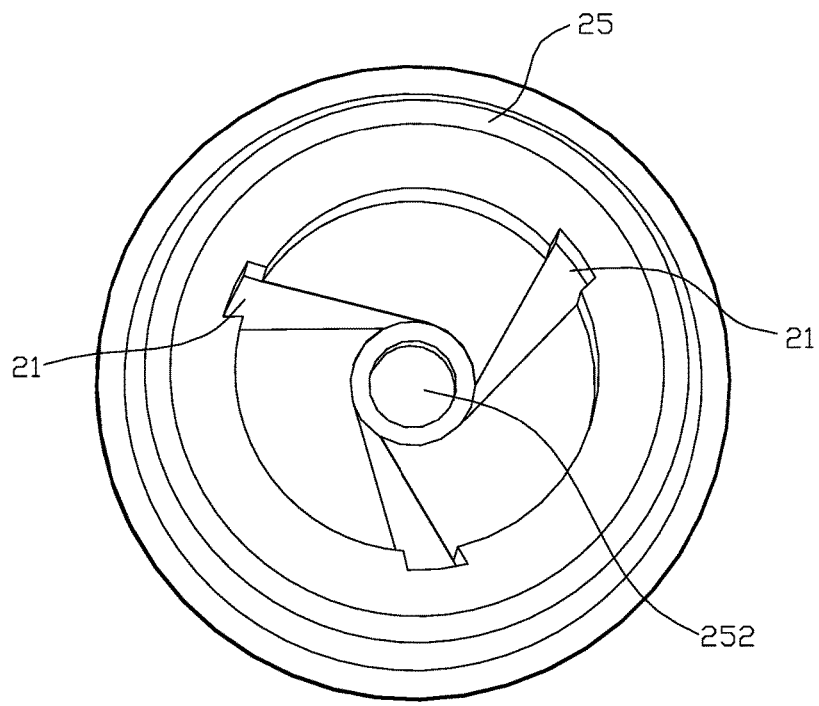
Figure 24:
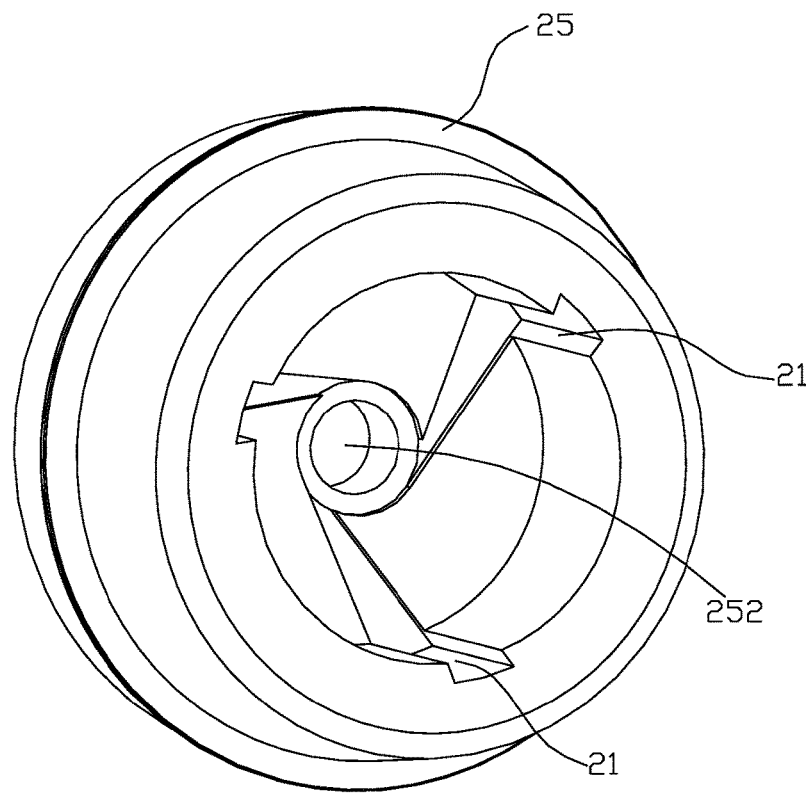

As shown in FIGS. 12 and 21, in another embodiment, the atomizing nozzle 2 comprises a nozzle housing 24 with an inner cavity 241, an inner core 25 deposited at the front section of the inner cavity 241, and a junction 27 inserted in the rear section of the inner cavity 241. Wherein, the junction 27 is connected with the water pump 5 by a transfusion tube 6, the spray port 23 is placed at the front end of the nozzle housing 24, the inner core is provided with a receiving hole, which is fixedly provided with a second block 29; as shown in FIGS. 23 and 24, the spiral channel 21 is placed at the inner wall of the inner core 25 and is located between the inner wall of the inner core 25 and the outer wall of the second block 29; the junction 27 is provided with a second through hole penetrated through forwards and backwards, and the second through hole 271 forms the fluid channel; as shown in FIG. 18, the front end of the inner core 25 is provided with an enlarging part of inner core 251 and a shrinking part of inner core 252 distributed successively along the front-rear direction; both the enlarging part of inner core 251 and the shrinking part of inner core 252 are cylindrical shapes, and the enlarging part of inner core 251 has a larger diameter than that of the shrinking part of inner core 252; all of the enlarging part of inner core 251, the shrinking part of inner core 252, the spray port 23 and the spiral channel 21 are communicated. In such embodiment, the pumped liquid from the water pump 5 successively flows through the second through hole 271, and the spiral channel 21 deposited a the inner wall of the inner core 25, to form spiral liquid flow when flowing though the spiral channel 21 at the inner wall of the inner core 25; the spiral liquid flow is pressed after flowing though the shrinking part of inner core 252 to enhance water pressure; and when the liquid enters the enlarging part of inner core 251 from the shrinking part of inner core 252, the water pressure of the pressed liquid is reduced, and finally liquid is radially sprayed. In order to make the atomizing nozzle 2 feature better atomization function, as shown in FIGS. 2 to 4, 8, 9, and 16, the nozzle housing 24 has a cylindrical external profile, the spray port 23 is circular, and the diameter of the spray port 23 is larger than that of the enlarging part of inner core 251; besides, as shown in FIGS. 5 to 7, 12, 13 and 18, the nozzle housing 24 may also have a trumpet-shaped external profile.

As shown in FIG. 21, the above junction 27 is provided with friction teeth 272 at the outer wall of the rear section, which guarantees that the junction 27 and the transfusion tube 6 features relative larger friction when connecting, thereby the connection strength therebetween is enhanced.

Figure 25:
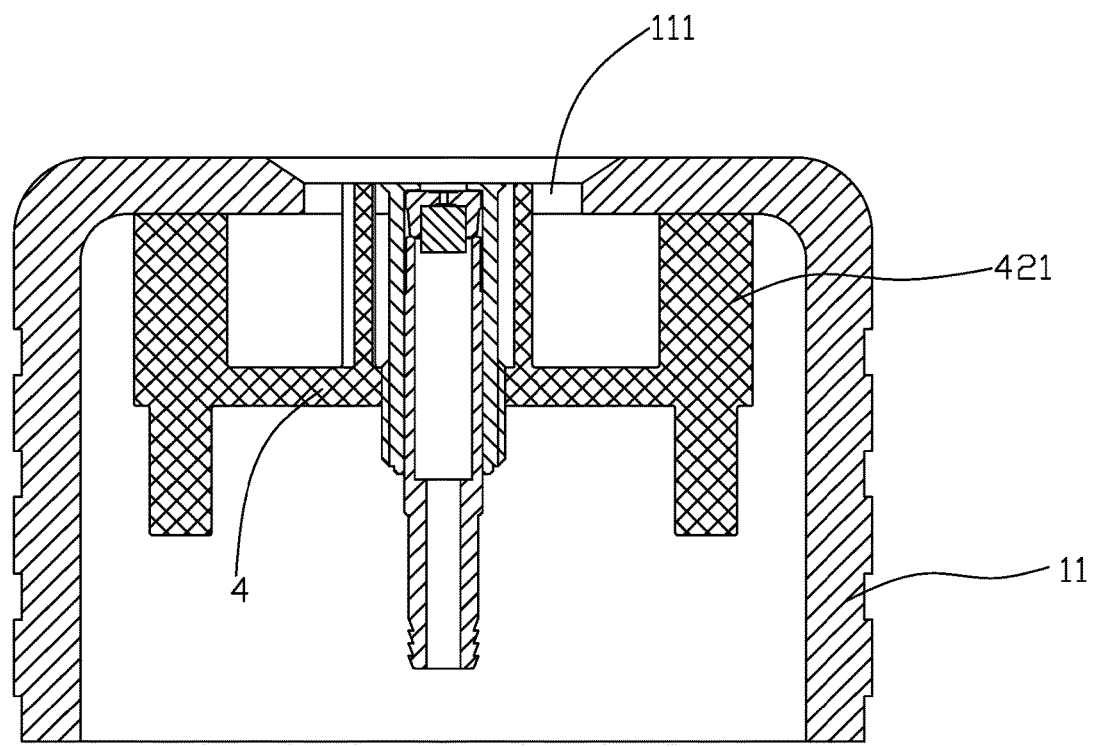
Figure 26:
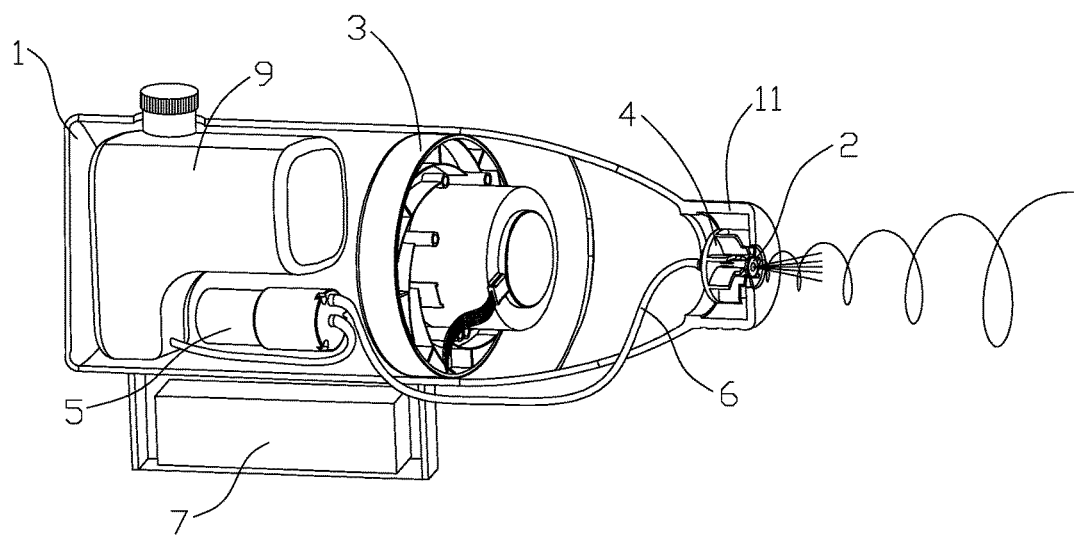

As shown in FIGS. 1 to 7, in the present invention, the air flow guide device 4 comprises a fixed disc 42, and the air flow guide blade 41 extends forward from the front end surface of the fixed disc 42; the nozzle housing 24 fixedly penetrates in the center of the fixed disc 42; the fixed disc 42 is provided with a plurality of connection parts 421, which are fixedly connected to the front port of the housing 1 by a fastener, e.g., a bolt or a screw, etc., as shown in FIG. 25, and the connection lid 11 is provided with an air outlet 111 at the front end. Meanwhile, as shown in FIG. 1, the connection lid 11 and the main body of the housing 1 is detachably connected. For ease of installation, as shown in FIGS. 8, 10, 12 and 14, the nozzle housing 24 of the atomizing nozzle 2 is threaded connected to the fixed disc 42 of the air flow guide device 4; for saving the mounting process, as shown in FIGS. 9, 11, 13 and 15, the nozzle housing 24 of the atomizing nozzle 2 is integrated with the fixed disc 42 of the air flow guide device 4.

For ease of carrying, and not being limited to the length of a power cable, the present invention adopts a battery for power supply. As shown in FIG. 1, the portable ultrafine nebulizer of the present invention further comprises a power supply battery 7 connected with the air turbine 3 and the water pump 5. Meanwhile, the power supply battery 7 is placed outside the housing 1, to facilitate the carrying of the power supply battery 7 in the backpack manner. Certainly, the carrying manner of the power supply battery 7 may also be portable, as shown in FIG. 26, the power supply battery 7 is installed on the outer side of the lower end of the housing 1. Since the present invention adopts an operating mode of a two-stage atomization, a relatively better atomizing effect is achievable if only a relative small air force is provided by the air turbine, so that the present invention requires for relatively lower power, but no necessity of carrying a relatively large battery, which avoids the problems of inconvenient to carry, etc., due to the relatively large size of the battery.

As shown in FIG. 22, the present invention provides a portable ultrafine nebulizer, comprising a housing 1 and an atomizing nozzle 2, an air pipe 8 fixed at the front port show the housing 1, an air turbine 3 deposited inside the housing 1, an air flow guide device 4 fixed at the front port of the air pipe 8, and a water pump 5 for pumping liquid; the atomizing nozzle 2 is placed at the front port of the air pipe 8, and the air flow guide device 4 is provided with a plurality of air flow guide blades 41 distributed uniformly around the atomizing nozzle 2, and each of the air flow guide blades 41 is provided with a guide surface 411; in the atomizing nozzle 2 is provided a spiral channel 21 and a fluid channel communicated with the water pump 5, the atomizing nozzle 2 is provided with a spray port 23 at the front end, and the spray port 23 is communicated with the fluid channel 21; the air turbine 3, the air flow guide blades 41 and the spray port 23 are distributed successively along the airflow direction. In the portable ultrafine nebulizer of the embodiment, the housing 1 is additionally provided with the air pipe 8 at the front port, and the air flow guide device 4 and the atomizing nozzle 2 are placed at the front port of the air pipe 8 simultaneously. As such, taking advantage that the air pipe 8 is easy to bend and invert, when in use, by controlling the direction of the front port of the air pipe 8, it is capable to randomly change the spray direction of the portable ultrafine nebulizer.

Therefore, the present invention effectively overcomes a variety of disadvantages in the prior art and has high industrial utility value.

The abovementioned embodiments only illustratively describe the principle and efficacy of the present invention, rather than being used to limit the present invention. Any person skilled in the art may modify or amend the abovementioned embodiments without departing from the spirit and scope of the present invention. Thus, all equivalent modifications or amendments accomplished by persons having common knowledge in the technical field concerned without departing from the spirit and technical thoughts revealed by the present invention shall still be covered by the claims of the present invention.

What is claimed is:

1. A portable ultrafine nebulizer comprising:
   a housing (1);
   an air turbine (3) and a water pump (5) located inside the housing (1);
   an atomizing means for atomizing water comprising anatomizing nozzle (2) and an air flow guide device (4);
   the atomizing nozzle (2) comprises a nozzle housing (24) with an inner cavity (241), an inner core (25) deposited at a front section of the inner cavity (241), a first block (26) deposited in the inner cavity (241) and located at a rear end of the inner core (25), and a junction (27) inserted in a rear section of the inner cavity (241), the junction (27) is connected with the water pump (5) by a transfusion tube (6), a spray port (23) is placed at a front end of the nozzle housing (24), an outer wall of the first block (26) is bonded to an inner wall of the nozzle housing (24);
   a liquid flow space is formed between an outer wall of the inner core (25) and an inner wall of the nozzle housing (24), and between a rear end of the inner core (25) and a front end of the first block (26), respectively; a spiral channel (21) is placed at the outer wall of the inner core (25), the first block (26) is provided with a first through hole (261) penetrated through forwards and backwards, the junction (27) is provided with a second through hole (271) penetrated through forwards and backwards; the first through hole (261), the second through hole (271) and the liquid flow space are communicated to form a fluid channel;
   the air flow guide device (4) comprises a connection lid (11) and a fixed disc (42) with a plurality of air flow guide blades (41) distributed uniformly around the atomizing nozzle (2), the air flow guide blades (41) extends forward from the fixed disc (42) into an inner chamber of the connection lid to define an air flow passage;
   wherein, the air flow passage comprises an inner chamber of the connection lid (11) having a ring shape entrance between the inner wall of the connection lid (11) and the fixed disc (42) and an air outlet (111) in a center part of bottom of the connection lid (11), a plurality of air flow guide ways created by the plurality of air flow guide blades (41) in the inner chamber;
   wherein, the nozzle housing (24) fixedly penetrates in a center of the fixed disc (42); the fixed disc (42) is provided with a plurality of connection parts (421), which are fixedly connected to the housing (1).

2. The portable ultrafine nebulizer according to claim 1, wherein the nozzle housing (24) has a spray port (23) which comprises an enlarging part (231), a shrinking part (232) and a collecting part (233) distributed successively along a front-rear direction; the enlarging part (231) is a conical shape with a gradually decrease diameter along the front-rear direction, both the shrinking part (232) and the collecting part (233) is cylindrical shapes extended along the front-rear direction; the collecting part (233) has a larger diameter than the shrinking part (232), a top of the inner cavity (241) is a conical shape with a gradually increase diameter along the front-rear direction, a front end of the nozzle housing (24) is provided with an annular groove (242) at a periphery of the enlarging part (231), and the groove (242) has a trapezoid cross section in the radial direction.

3. The portable ultrafine nebulizer according to claim 1, wherein the nozzle housing (24) of the atomizing nozzle (2) is threaded connected to the fixed disc (42) of the air flow guide device (4), or is integral with the fixed disc (42) of the air flow guide device (4).

4. The portable ultrafine nebulizer according to claim 1, wherein the nebulizer further comprises a power supply battery (7) connected with the air turbine (3) and the water pump (5), and the power supply battery (7) is placed outside the housing (1).

5. The portable ultrafine nebulizer according to claim 1, wherein the nozzle housing (24) has a trumpet-shaped external profile.

\* \* \* \* \*